(12) United States Patent
Tsujita

(10) Patent No.: US 9,835,477 B2
(45) Date of Patent: Dec. 5, 2017

(54) WHEEL ASSEMBLY ROTATIONAL POSITION IDENTIFYING APPARATUS

(71) Applicant: PACIFIC INDUSTRIAL CO., LTD., Ogaki-shi, Gifu-ken (JP)

(72) Inventor: Yasuhisa Tsujita, Motosu (JP)

(73) Assignee: PACIFIC INDUSTRIAL CO., LTD., Ogaki-Shi, Gifu-Ken (JP)

( * ) Notice: Subject to any disclaimer, the term of this patent is extended or adjusted under 35 U.S.C. 154(b) by 0 days.

(21) Appl. No.: 15/115,014

(22) PCT Filed: Sep. 17, 2015

(86) PCT No.: PCT/JP2015/076549
§ 371 (c)(1),
(2) Date: Jul. 28, 2016

(87) PCT Pub. No.: WO2017/046922
PCT Pub. Date: Mar. 23, 2017

(65) Prior Publication Data
US 2017/0227382 A1 Aug. 10, 2017

(51) Int. Cl.
*G01N 27/22* (2006.01)
*G01D 5/244* (2006.01)
(Continued)

(52) U.S. Cl.
CPC .............. *G01D 5/244* (2013.01); *B60C 23/00* (2013.01); *B60C 29/005* (2013.01); *G01N 27/22* (2013.01)

(58) Field of Classification Search
CPC .................................. G01V 7/04; B60C 23/042
See application file for complete search history.

(56) References Cited

U.S. PATENT DOCUMENTS

2003/0090373 A1  5/2003  Bergerhoff et al.
2003/0156022 A1* 8/2003  Saheki ................ B60C 23/0408
                                                340/442
(Continued)

FOREIGN PATENT DOCUMENTS

JP  2009226966 A  10/2009
JP  2010122023 A   6/2010
(Continued)

OTHER PUBLICATIONS

International Search Report, PCT/JP2015/076549, dated Nov. 24, 2015, pp. 2.
(Continued)

*Primary Examiner* — Giovanni Astacio-Oquendo
*Assistant Examiner* — Alvaro Fortich
(74) *Attorney, Agent, or Firm* — Cantor Colrburn LLP

(57) ABSTRACT

A wheel assembly rotational position identifying apparatus includes an acceleration detector, a control section, and a battery. The control section identifies the rotational position of the wheel assembly based on an acceleration detected by the acceleration detector. The control section operates in a control mode that is a selected one of a normal mode and a power saving mode, in which a power consumption associated with identification of the rotational position of the wheel assembly is smaller than that in the normal mode. The control section switches the control mode to the normal mode when an initiation condition is met in accordance with an input from outside. The control section also switches the control mode to the power saving mode when a termination condition is met in the normal mode.

7 Claims, 4 Drawing Sheets

(51) Int. Cl.
  *B60C 29/00*  (2006.01)
  *B60C 23/00*  (2006.01)

(56) References Cited

U.S. PATENT DOCUMENTS

| | | | |
|---|---|---|---|
| 2007/0144248 A1* | 6/2007 | Okubo | B60C 23/0432 |
| | | | 73/146.4 |
| 2009/0237228 A1 | 9/2009 | Watabe | |
| 2014/0150543 A1 | 6/2014 | Shima et al. | |
| 2014/0340213 A1* | 11/2014 | Okada | B60C 23/0416 |
| | | | 340/444 |

FOREIGN PATENT DOCUMENTS

| | | |
|---|---|---|
| JP | 201251499 A | 3/2012 |
| JP | 2012051499 A | 3/2012 |
| JP | 2012236556 A | 12/2012 |
| JP | 2014227124 A | 12/2014 |

OTHER PUBLICATIONS

Received the Korean Intellectual Property Office; Office Action (Notification of Reason for Refusal) dated Sep. 20, 2017, during the prosecution of the corresponding Korean patent application 10-2016-7015798.

* cited by examiner

WHEEL ASSEMBLY ROTATIONAL POSITION IDENTIFYING APPARATUS

TECHNICAL FIELD

The present invention relates to a wheel assembly rotational position identifying apparatus that is provided in a wheel assembly of a vehicle and identifies the rotational position of the wheel assembly.

BACKGROUND ART

A vehicle body has wheel assemblies, each of which includes a vehicle wheel and a tire attached to the wheel. Each wheel assembly is provided with a tire condition detecting apparatus, which detects the condition of the tire such as the air pressure and the temperature in the tire. Each tire condition detecting apparatus has a function of transmitting a signal indicating the detected tire condition. When the receiver mounted on the vehicle receives signals from the tire condition detecting apparatuses, a display displays the conditions of the respective tires based on the signals. Since each tire condition detecting apparatus is attached to a wheel assembly, the apparatus incorporates a battery to supply power.

For example, Patent Document 1 discloses a tire condition detecting apparatus that has a function of identifying the rotational position of a wheel assembly at a predetermined interval and transmits a signal corresponding to the rotational position of the wheel assembly. The vehicle has angle sensors provided at positions corresponding to the wheel assemblies to detect the rotational positions (the rotational angular positions) of the wheel assemblies. When the receiver receives signals transmitted from the tire condition detecting apparatuses, the rotational positions of the wheel assemblies obtained from the signals are checked against the rotational positions detected by the angle sensors. This allows each condition detecting apparatus, which is the source of a signal, to be identified as the one provided in a specific wheel assembly.

PRIOR ART DOCUMENT

Patent Document

Patent Document 1: Japanese Laid-Open Patent Publication No. 2010-122023

SUMMARY OF THE INVENTION

Problems that the Invention is to Solve

It is desired to reduce the power consumption of tire condition detecting apparatuses to extend the life of the batteries incorporated in the apparatuses.

Accordingly, it is an objective of the present invention to provide a wheel assembly rotational position identifying apparatus that is configured to reduce power consumption.

Means for Solving the Problems

To achieve the foregoing objective and in accordance with one aspect of the present invention, a wheel assembly rotational position identifying apparatus is provided, which is provided in a wheel assembly of a vehicle to identify a rotational position of the wheel assembly. The apparatus includes an acceleration detector, which is configured to detect an acceleration that changes in accordance with the rotational position of the wheel assembly, a control section, which is configured to identify the rotational position of the wheel assembly based on the acceleration detected by the acceleration detector, and a battery, which is a power source for the wheel assembly rotational position identifying apparatus. The control section is configured to operate in a control mode that is a selected one of a normal mode, in which the rotational position of the wheel assembly is allowed to be identified, and a power saving mode, in which a power consumption associated with identification of the rotational position of the wheel assembly is smaller than that in the normal mode. The control section is configured to switch the control mode to the normal mode when an initiation condition is met in accordance with an input from outside. The control section is configured to switch the control mode to the power saving mode when a termination condition is met in the normal mode.

With this configuration, when the termination condition is met in the normal mode, the control mode is switched to the power saving mode, in which power consumption associated with identification of the rotational position of the wheel assembly is less than that in the normal mode. This reduces the power consumption associated with identification of the rotational position of the wheel assembly. When the wheel assembly rotational position identifying apparatus receives an input, the control mode is switched to the normal mode.

The above described wheel assembly rotational position identifying apparatus may be configured such that the termination condition is met when a specified time has elapsed since the vehicle started moving.

With this configuration, the control mode is switched from the normal mode to the power saving mode when the specified time has elapsed since the vehicle started moving. This reduces the power consumption.

The above described wheel assembly rotational position identifying apparatus may include a property detector, which is configured to detect an electrical property of a valve stem provided in the wheel assembly, and may be configured such that the initiation condition is met in response to an amount of change in the electrical property of the valve stem detected by the property detector exceeding a reference change amount.

With this configuration, the control mode is switched to the normal mode to identify the rotational position of the wheel assembly if the worker touches the valve stem when replacing the tire and the amount of change in the electrical property of the valve stem exceeds a reference change amount. Particularly, when it is possible to identify in which wheel assembly the wheel assembly rotational position identifying apparatus is located based on the rotational position of the wheel assembly identified by the wheel assembly rotational position identifying apparatus, it is possible to reliably determine in which wheel assembly the wheel assembly rotational position identifying apparatus is located when the vehicle is moved after the tire is replaced.

The above described wheel assembly rotational position identifying apparatus may be configured such that the control section is configured to execute a process based on an input from outside when the vehicle is in a stopped state, and that the control section is configured not to execute a process based on an input from outside when the vehicle is moving.

With this configuration, since the tire is replaced when the vehicle is in a stopped state, the control mode is switched to the normal mode by executing a process based on an external input during a stopped state of the vehicle. Since tire replacement is never performed when the vehicle is moving, no process based on an external input is executed when the vehicle is moving. The power consumption is reduced, accordingly.

The above described wheel assembly rotational position identifying apparatus may be configured such that the control section is configured to execute a detection process through the property detector when the vehicle is in a stopped state, and that the control section is configured not to execute the detection process through the property detector when the vehicle is moving.

The above described wheel assembly rotational position identifying apparatus may be configured such that the control section is configured to identify the rotational position of the wheel assembly less frequently in the power saving mode than in the normal mode.

The above described wheel assembly rotational position identifying apparatus may be configured such that the control section is configured not to identify the rotational position of the wheel assembly in the power saving mode.

EFFECTS OF THE INVENTION

The present invention reduces the power consumption of the wheel assembly rotational position identifying apparatus.

MODES FOR CARRYING OUT THE INVENTION

One embodiment of the present invention will now be described.

Figure 1:
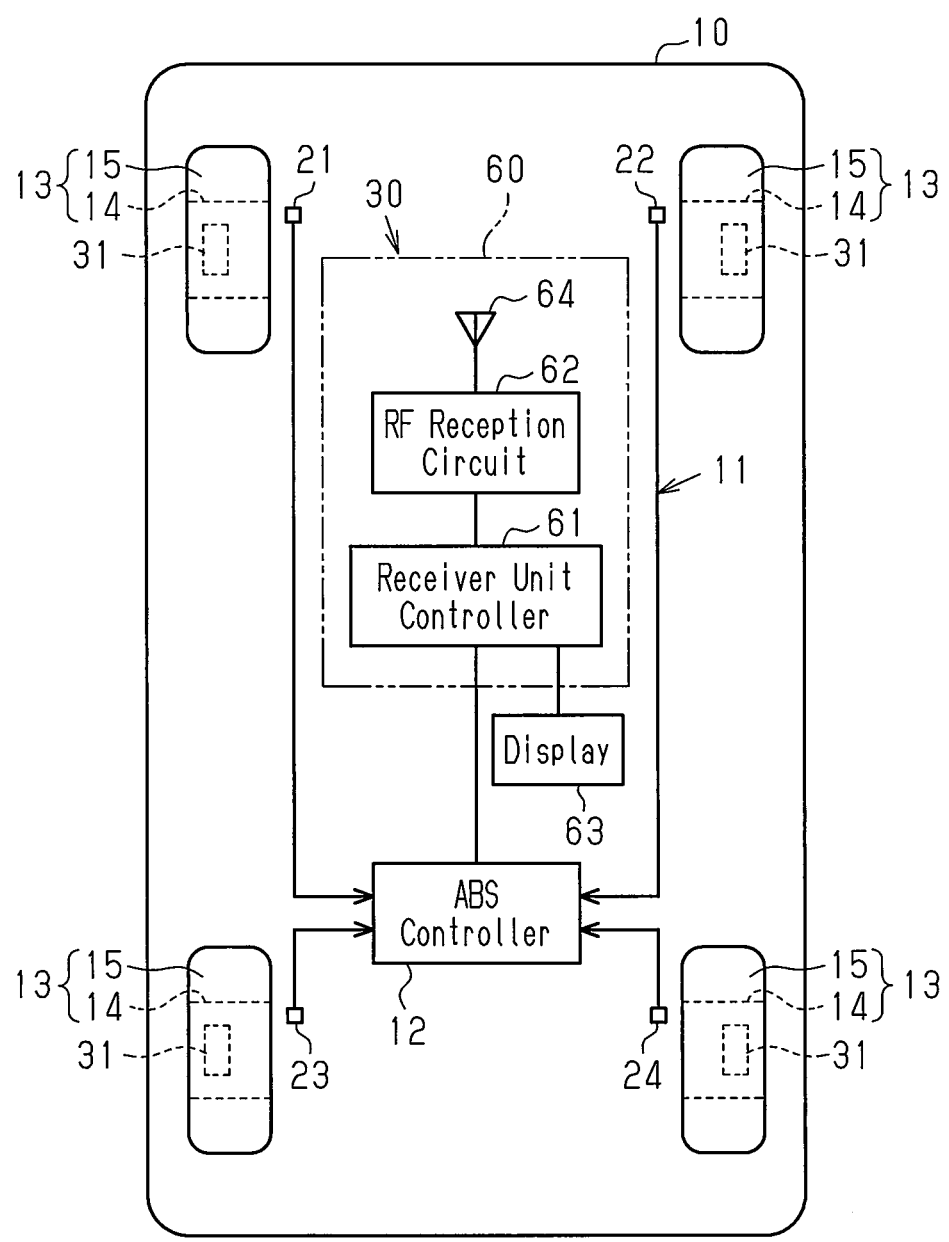
FIG. 1 is a schematic diagram illustrating a vehicle on which sensor units according to one embodiment are mounted.

As shown in FIG. 1, a vehicle 10 has four wheel assemblies 13, an anti-lock brake system (ABS) 11, and a tire condition monitoring apparatus 30. Each wheel assembly 13 includes a vehicle wheel 14 and a tire 15 attached to the vehicle wheel 14.

The tire condition monitoring apparatus 30 includes sensor units 31, which are attached to the respective wheel assemblies 13, and a receiver unit 60, which is arranged in the body of the vehicle 10.

The ABS 11 includes an ABS controller 12 and rotation sensor units 21 to 24, each of which corresponds to one of the four wheel assemblies 13 of the vehicle 10. The ABS controller 12 includes a microcomputer, that is, a processor, and obtains the rotational positions (rotation angular positions) of the wheel assemblies 13 based on signals from the rotation sensor units 21 to 24.

Figure 2:
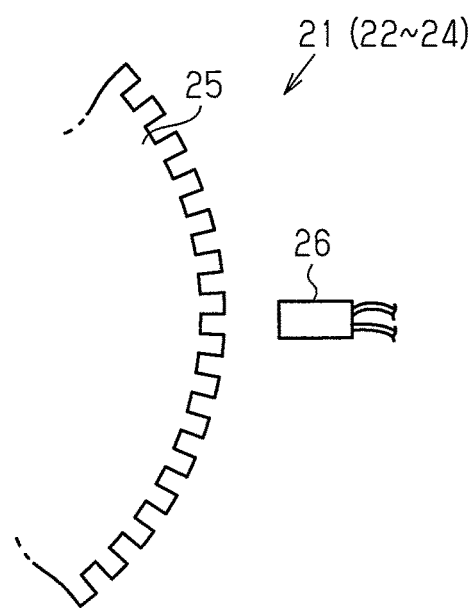
FIG. 2 is a schematic diagram showing a rotation sensor unit of the embodiment.

As shown in FIG. 2, each of the rotation sensor units 21 to 24 is located in the vicinity of a wheel assembly 13 and on an unsprung component, and includes a gear 25, which rotates integrally with the wheel assembly 13, and a detector 26, which is arranged to face the outer circumferential surface of the gear 25. The gear 25 has multiple teeth (forty-eight teeth in the present embodiment) at equal angular intervals on the outer circumferential surface. The detector 26 detects pulse signals generated by rotation of the gear 25. The ABS controller 12 is connected to each detector 26 by a wire and obtains the rotational position of each wheel assembly 13 based on a count value of pulses of the corresponding detector 26.

Figure 3:
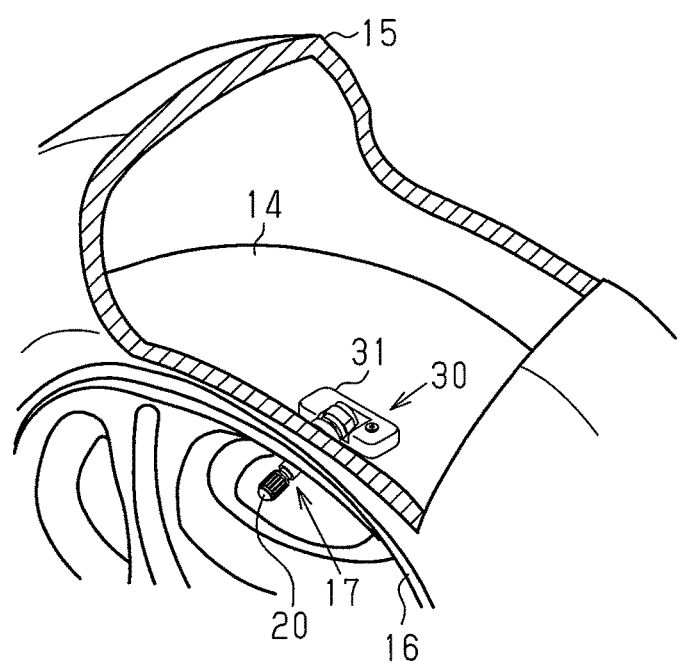
FIG. 3 is a perspective view illustrating a state in which a tire valve of the embodiment is attached to a rim.

As shown in FIG. 3, each wheel 14 has a rim 16, to which a tire valve 17 is attached. A sensor unit 31 is attached to and integrated with the tire valve 17 to be arranged in the tire 15 attached to the vehicle wheel 14.

Figure 4:
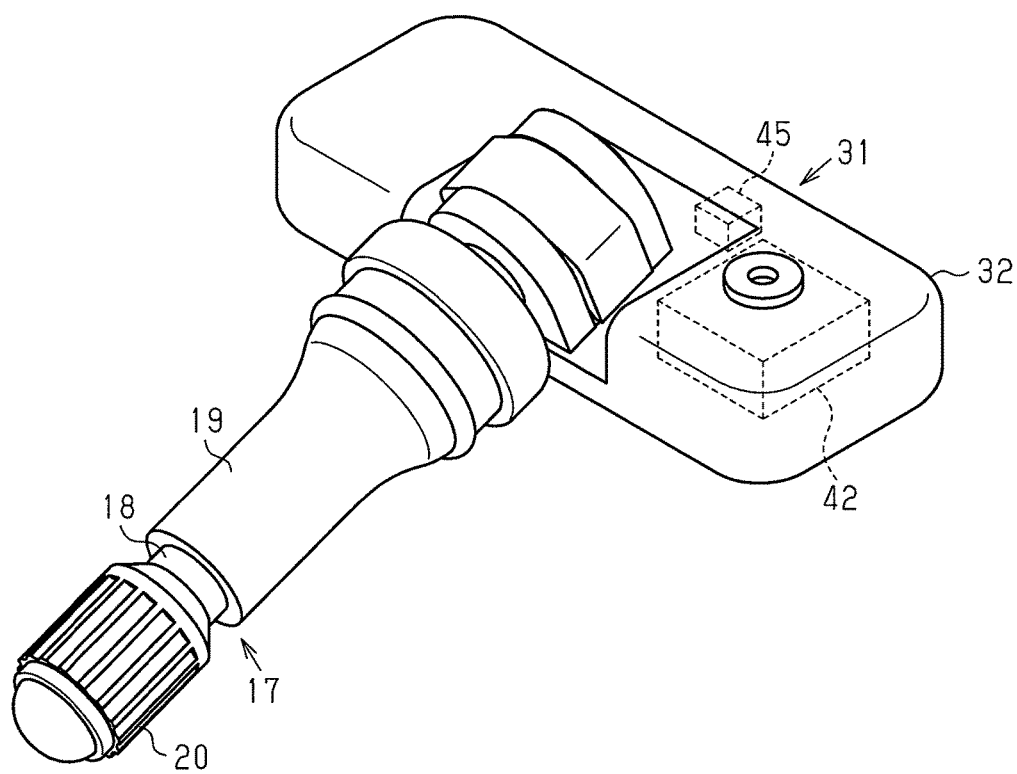
FIG. 4 is a perspective view showing the tire valve and the sensor unit of the embodiment.

As shown in FIG. 4, the tire valve 17 includes a cylindrical metal valve stem 18 and a rubber body 19, which is attached to the outer circumferential surface of the valve stem 18. The valve stem 18 has an introduction passage (not shown). A valve mechanism (not shown) is incorporated in the distal portion of the valve stem 18, and a cap 20 is attached to the distal end of the valve stem 18.

A housing 32 of the sensor unit 31 accommodates electronic components such as a pressure sensor 42 and a capacitance sensor 45, a battery, and an antenna. The pressure sensor 42 detects the pressure of the tire 15. The capacitance sensor 45 is electrically connected to the tire valve 17 to detect the capacitance of the tire valve 17.

Figure 5:
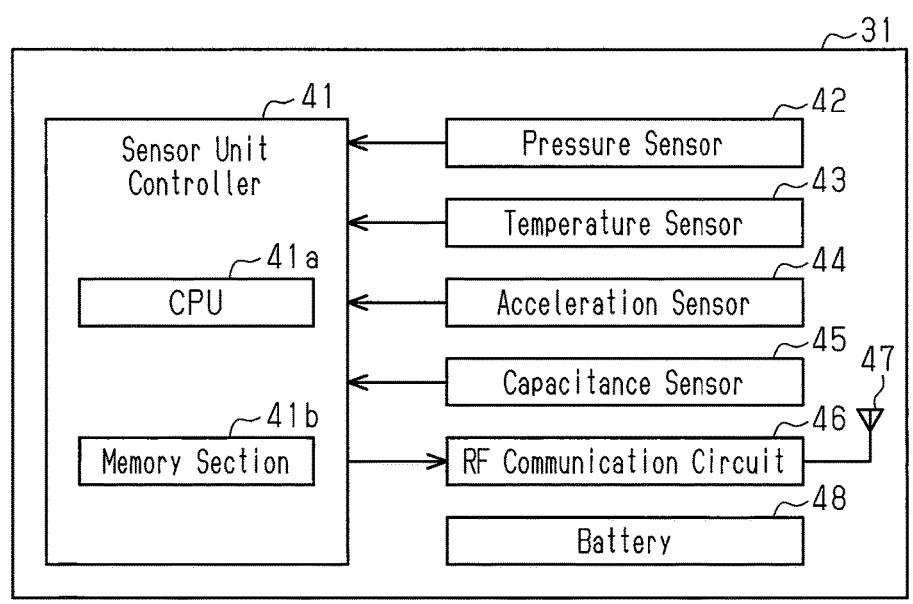
FIG. 5 is a block diagram illustrating the electrical configuration of the sensor unit of the embodiment.

As shown in FIG. 5, each sensor unit 31 includes, in the housing 32, a sensor unit controller 41, a pressure sensor 42, a temperature sensor 43, an acceleration sensor 44, a capacitance sensor 45, an RF communication circuit 46, an RF antenna 47, and a battery 48. The sensor unit 31 is driven by power supplied by the battery 48.

The pressure sensor 42 detects the air pressure in the tire 15. The temperature sensor 43 detects the temperature in the tire 15. The acceleration sensor 44, which is an acceleration detector, rotates integrally with the wheel assembly 13 to detect the acceleration acting on the acceleration sensor 44. The capacitance sensor 45, which is a property detector, detects the capacitance of the valve stem 18 of the tire valve 17. The RF communication circuit 46 transmits and receives signals via the RF antenna 47 by using radio waves in a frequency band of an ultra-high frequency (2.4 GHz in the present embodiment).

The sensor unit controller 41 is a control circuit or a processor, which is constituted by a microcomputer having a CPU 41a, a memory section 41b (such as a RAM and a ROM), and an input-output port. The memory section 41b of the sensor unit controller 41 stores programs for controlling operation of the sensor unit 31 in an integrated manner. In the memory section 41b, an ID code is registered, which is identification information unique to each sensor unit 31. The ID code is information used to identify each sensor unit 31 at the receiver unit 60. The sensor unit controller 41 functions as a control section.

The sensor unit controller 41, specifically, the CPU 41a, obtains, at a predetermined obtainment interval, the tire air pressure detected by the pressure sensor 42, the tire internal temperature detected by the temperature sensor 43, and the acceleration (gravitational acceleration) detected by the acceleration sensor 44.

The sensor unit controller 41 is capable of detecting the rotational position (the rotation angular position) of the wheel assembly 13 based on an acceleration signal from the acceleration sensor 44, referring to the relationship between the acceleration acting on the sensor unit 31, specifically, the acceleration sensor 44 and the position of the sensor unit 31. The acceleration acting on the acceleration sensor 44, that is, the acceleration detected by the acceleration sensor 44 changes in accordance with the rotational position of the wheel assembly 13. For example, the sensor unit 31 is configured such that, when the acceleration sensor 44 detects an acceleration of +1 G, the sensor unit 31 is located at the lowest position in the wheel assembly 13. Thus, when the acceleration sensor 44 detects an acceleration of +1 G, the sensor unit controller 41 detects that the wheel assembly 13 is at a rotational position at which the sensor unit 31 is located at the lowest position in the wheel assembly 13. The sensor unit 31, which includes a sensor unit controller 41 and an acceleration sensor 44, functions as a wheel assembly rotational position identifying apparatus, which is provided in each wheel assembly 13 of the vehicle 10 to identify the rotational position of the wheel assembly 13.

The sensor unit controller 41 is capable of determine whether the vehicle 10 is moving based on an acceleration signal from the acceleration sensor 44. For example, the sensor unit controller 41 is capable of determining that the vehicle 10 is moving when the acceleration detected by the acceleration sensor 44 changes in a predetermined range (for example, a range from −1 G to +1 G).

When a predetermined output condition is met, the sensor unit controller 41 outputs, to the RF communication circuit 46, transmission data that contains the tire air pressure data, the tire internal temperature data, and the ID code. The RF communication circuit 46 generates a transmission signal by modulating the transmission data output from the sensor unit controller 41, and wirelessly transmits the transmission signal from the RF antenna 47.

In the present embodiment, the output condition is that, while the vehicle 10 is moving, the wheel assembly 13 is detected to be at the rotational position at which the sensor unit 31 is located at the lowest position in the wheel assembly 13. The output condition may include determination that the tire air pressure or the tire internal temperature is abnormal.

When determining that the vehicle 10 is in a stopped state, the sensor unit controller 41 identifies the capacitance of the valve stem 18 of the tire valve 17 based on a signal from the capacitance sensor 45 and stores capacitance data indicating the identified capacitance in the memory section 41b. In the present embodiment, the sensor unit controller 41 performs a series of processes for identifying the capacitance and storing the capacitance data for approximately 1 ms at a predetermined interval (for example, 1 s).

The sensor unit controller 41 determines whether the amount of change in the identified capacitance of the valve stem 18 has exceeded a predetermined reference change amount. When the tire 15 is replaced, the worker touches the valve stem 18 of the tire valve 17. Thus, the reference change amount is defined as the amount of change in the capacitance at which it is possible to assume that the worker has touched the valve stem 18.

When determining that the vehicle 10 is moving based on the acceleration signal from the acceleration sensor 44, the sensor unit controller 41 does not execute the process for identifying the capacitance of the valve stem 18 of the tire valve 17.

As shown in FIG. 1, the receiver unit 60 includes a receiver unit controller 61, an RF reception circuit 62, and a reception antenna 64. A display 63 is connected to the receiver unit controller 61. The receiver unit controller 61 is a processor, which is constituted by a microcomputer including a CPU and a memory section (such as a ROM and a RAM). The memory section stores programs for controlling operation of the receiver unit 60 in an integrated manner.

The RF reception circuit 62 demodulates signals delivered from the sensor units 31 via the reception antenna 64 and delivers the demodulated signals to the receiver unit controller 61.

Based on a signal demodulated by the RF reception circuit 62, the receiver unit controller 61 identifies the condition of the tire 15 (the tire air pressure and the tire internal temperature) that corresponds to the sensor unit 31 that is the source of the signal. The receiver unit controller 61 causes the display 63 to show information regarding the conditions of the tires 15.

The receiver unit controller 61 is connected to the ABS controller 12 and receives pulse signals generated by the rotation sensor units 21 to 24 via the ABS controller 12. Based on the pulse signals, the receiver unit controller 61 identifies the rotational positions of the wheel assemblies 13.

When the RF reception circuit 62 receives a signal transmitted from any of the sensor units 31, the receiver unit controller 61 identifies the rotational position of the corresponding wheel assembly 13 at the time of the reception of the transmission signal by the RF reception circuit 62 based on the transmission signal from the sensor unit 31. In the present embodiment, each sensor unit 31 transmits a signal when located at the lowest position in the corresponding wheel assembly 13. Thus, the rotational position of the wheel assembly 13 at the time of reception of the transmission signal from the sensor unit 31 by the RF reception circuit 62 is the rotational position at which the sensor unit 31 is located at the lowest position in the wheel assembly 13.

The receiver unit controller 61 compares the rotational position of the wheel assembly 13 that has been identified based on the transmission signal from the sensor unit 31 with the rotational positions of the wheel assemblies 13 that have been identified based on the pulse signals from the rotation sensor units 21 to 24, thereby identifying the wheel assembly 13 that corresponds to the sensor unit 31 having transmitted the signal. That is, it is possible to identify to which wheel assembly 13 the sensor unit 31 that is the source of the signal is attached based on the rotational position of the wheel assembly 13 that has been identified based on the transmission signal from the sensor unit 31 and the rotational positions of the wheel assemblies 13 detected by the rotation sensor units 21 to 24.

In the present embodiment, each sensor unit controller 41 is capable of setting, as the control mode, either one of a normal mode and a power saving mode, in which power consumption associated with identification of the rotational position of the wheel assembly 13 is reduced compared to that in the normal mode. The sensor unit controller 41 sets the control mode by setting, as a control mode flag assigned to the memory section 41b, either a value indicating the normal mode or a value indicating the power saving mode.

In the normal mode of the present embodiment, the sensor unit controller 41 identifies the rotational position of the wheel assembly at a specified interval when the vehicle 10 is moving, and transmits a signal indicating the condition of the tire in correspondence with the identified rotational position of the wheel assembly. That is, when the identified rotational position of the wheel assembly 13 is at the rotational position at which the sensor unit 31 is located at the lowest position in the wheel assembly 13, the sensor unit controller 41 transmits a signal indicating the condition of the tire. In the power saving mode, the sensor unit controller 41 does not identify the rotational position of the wheel assembly regardless of whether the vehicle 10 is moving or in a stopped state.

Figure 6:
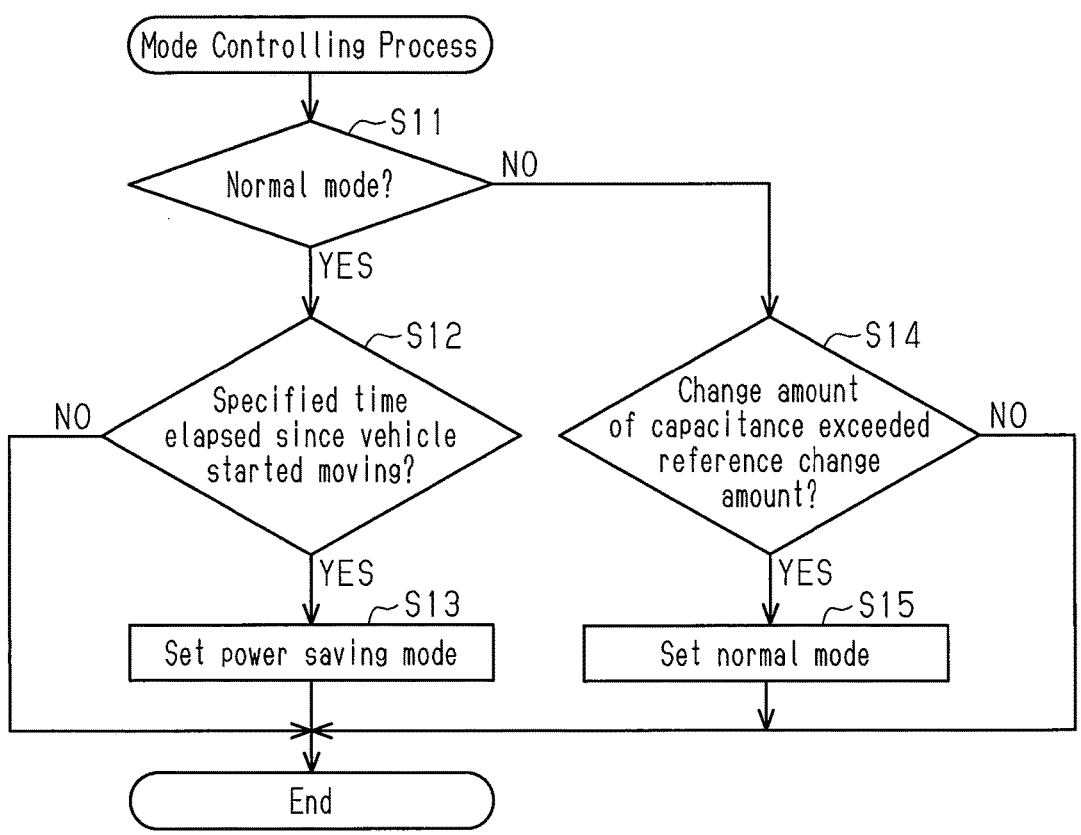
FIG. 6 is a flowchart showing a mode controlling process of the sensor unit of the embodiment.

With reference to FIG. 6, a mode controlling process, which is executed by each sensor unit controller 41 at a predetermined interval, will now be described.

First, as shown in FIG. 6, the sensor unit controller 41 reads out the value of the control mode flag, which has been assigned to the memory section 41b. Based on the value, the sensor unit controller 41 determines whether the control mode is the normal mode (step S11). If it is determined that the control mode is the normal mode, the sensor unit controller 41 determines whether a specified time has elapsed since the vehicle 10 started moving (step S12). If it is determined that the specified time has elapsed since the vehicle 10 started moving in the normal mode, the sensor unit controller 41 sets the control mode flag assigned to the memory section 41b to a value indicating the power saving mode, thereby setting the control mode to the power saving mode (step S13). If it is determined that the specified time has not elapsed since the vehicle 10 started moving in the normal mode, the sensor unit controller 41 ends the mode controlling process without executing step S13.

If it is determined that the control mode is not the normal mode (that is, if the control mode is determined to be the power saving mode), the sensor unit controller 41 determines whether the amount of change in the capacitance has exceeded a reference change amount (step S14). If it is determined that the change amount of the capacitance has exceeded the reference change amount, the sensor unit controller 41 sets the control mode flag assigned to the memory section 41b to a value indicating the normal mode, thereby setting the control mode to the normal mode (step S15). If it is determined that the change amount of the capacitance has not exceeded the reference change amount in the power saving mode, the sensor unit controller 41 ends the mode controlling process without executing step S15.

The initiation condition for the normal mode (that is, the termination condition for the power saving mode) is met when the change amount of the capacitance of the valve stem 18 exceeds the reference change amount. In contrast, the termination condition for the normal mode (that is, the initiation condition for the power saving mode) is met when the specified time has elapsed since it was determined that the vehicle 10 started moving in the normal mode.

Operation of each sensor unit 31 according to the present embodiment will now be described.

First, the sensor unit 31 identifies the rotational position of the wheel assembly at a specified interval when the vehicle is moving in the normal mode. When the rotational position of the wheel assembly 13 is identified as the position at which the sensor unit 31 is located at the lowest position in the wheel assembly 13, the sensor unit 31 transmits a signal indicating the condition of the tire. In contrast, in the power saving mode, the rotational position of the wheel assembly is not identified, and no signal indicating the condition of the tire is transmitted. However, even in the power saving mode, if the tire air pressure or the tire internal temperature is determined to be abnormal, a signal indicating the tire condition is transmitted. When the vehicle 10 is moving, the process for identifying the capacitance of the valve stem 18 is not executed. The process for identifying the capacitance of the valve stem 18 is executed when the vehicle 10 is in a stopped state.

When the specified time has elapsed since the vehicle 10 started moving in the normal mode, the control mode is switched from the normal mode to the power saving mode. When the amount of change in the capacitance of the valve stem 18 has exceeded the reference change amount in the power saving mode, it is assumed that a worker has touched the valve stem 18 during tire replacement. In this case, the control mode is switched to the normal mode.

The above described embodiment has the following advantages.

(1) When the termination condition is met in the normal mode, the control mode is switched to the power saving mode, in which power consumption associated with identification of the rotational position of each wheel assembly 13 is less than that in the normal mode. This reduces the power consumption associated with identification of the rotational position of each wheel assembly 13.

(2) The control mode is switched to the normal mode to identify the rotational position of each wheel assembly 13 if the worker touches the valve stem 18 when replacing the tire 15 and the amount of change in the electrical property of the valve stem 18 exceeds the reference change amount. In other words, when the sensor unit 31 receives any input from the outside, the control mode is switched to the normal mode. Particularly, in the present embodiment, it is possible to identify in which of the wheel assemblies 13 the sensor unit 31 is provided based on the rotational position of the wheel assembly 13 identified by the sensor unit 31 and the rotational positions of the wheel assemblies 13 detected by the rotation sensor units 21 to 24. Thus, it is possible to reliably determine in which wheel assembly 13 each sensor unit 31 is provided when the vehicle 10 is caused to move after replacement of the tire 15.

(3) In the normal mode, each sensor unit 31 transmits a signal when the corresponding wheel assembly 13 is at a specific rotational position. However, in the power saving mode, the sensor unit 31 does not transmit a signal even when the wheel assembly 13 is at the specific rotational position. Thus, when the control mode is switched to the power saving mode, the power consumption associated with signal transmission is reduced.

(4) The RF communication circuit 46 uses radio waves in a frequency band of an ultra-high frequency. In this case, the power consumption is greater than in a case in which radio waves in a frequency band of a very high frequency are used. However, switching the control mode to the power saving mode reduces the power consumption associated with signal transmission.

(5) When the control mode is switched to the normal mode, the control can be executed in the normal mode until the specified time elapses after the vehicle 10 starts moving, and the rotational position of each wheel assembly 13 can be identified. The lapse of the specified time allows the control mode to be switched from the normal mode to the power saving mode, thus reducing the power consumption.

(6) Since the tires 15 are replaced when the vehicle 10 is in a stopped state, the control mode can be switched to the normal mode by identifying the capacitance of the valve stems 18 in a stopped state of the vehicle 10. Since tire replacement is never performed when the vehicle 10 is moving, no identification of the capacitances of the valve stems 18 is executed when the vehicle 10 is moving. The power consumption is reduced, accordingly.

(7) When the vehicle 10 is moving in the normal mode, the rotational position of each wheel assembly 13 is identified. However, when the vehicle 10 is in a stopped state, the rotational position of each wheel assembly 13 is not identified. This reduces the power consumption associated with the identification of the rotational position of each wheel assembly 13.

The embodiment may be modified as follows.

The initiation condition of the normal mode may be met when the vehicle 10 starts moving after the amount of change in the capacitance of each valve stem 18 exceeds the reference change amount.

In the power saving mode, as long as the power consumption is lower than that in the normal mode, each sensor unit 31 may identify the rotational position of the corresponding wheel assembly 13 when the vehicle 10 is moving and transmit information indicating the identified rotational position of the wheel assembly 13. According to a specific example, in the normal mode, the rotational position of each wheel assembly is identified at a first specified interval when the vehicle 10 is moving. In the power saving mode, the rotational position of each wheel assembly is identified at a second specified interval, which is longer than the first interval, when the vehicle 10 is moving. In other words, it suffices if the rotational position of the wheel assembly is identified less frequently in the power saving mode than in the normal mode.

Each sensor unit 31 may identify the rotational position of the corresponding wheel assembly 13 when the vehicle 10 is in a stopped state and transmit information indicating the identified rotational position of the wheel assembly 13.

Each sensor unit 31 may execute determination regarding the capacitance of the corresponding valve stem 18 while the vehicle 10 is moving. That is, the sensor unit 31 may execute determination regarding the capacitance of the valve stem 18 regardless of whether the vehicle is in a stopped state or is moving.

Each sensor unit 31 may transmit a signal when the corresponding wheel assembly 13 is at a rotational position at which the sensor unit 31 is located at the highest position in the wheel assembly 13.

Each sensor unit 31 transmits signals using radio waves in a frequency band of an ultra-high frequency. However, each sensor unit 31 may transmit signals using radio waves in a frequency band of a frequency other than an ultra-high frequency.

Each sensor unit 31 is capable of transmitting and receiving signals. However, each sensor unit 31 may be configured not to receive signals. The sensor unit 31 may lack the function of transmitting information indicating the rotational position of the corresponding wheel assembly.

Each sensor unit 31 may switch the control mode to the normal mode in response to the measurement result of the complex impedance including an inductance and a resistance value. That is, it suffices if the electrical property of the tire valve 17 can be detected so that it can be assumed that the tire valve 17 has been touched at replacement of the tire 15.

Each sensor unit 31 may switch the control mode to the normal mode in response to a signal delivered from the outside, for example, from the receiver unit 60 or a trigger signal transmitter (not shown). In such a case, the sensor unit 31 may be configured without the capacitance sensor 45 in it.

Regardless of the time elapsed since the vehicle 10 started moving, the termination condition of the normal mode may be met in accordance with other factors such as reception of an external signal by the sensor unit 31. Alternatively, the termination condition of the normal mode may be met in accordance with a combination of these factors.

Each sensor unit 31 detects, as the condition of the tire, the air pressure and the temperature in the tire. However, each sensor unit 31 may detect either one of these parameters. Alternatively, each sensor unit 31 may detect other parameters such as the wear of the tire. That is, each sensor unit 31 preferably functions as a tire condition detecting apparatus, which detects the condition of the tire, and a wheel assembly rotational position identifying apparatus, which identifies the rotational position of the wheel assembly.

The sensor units 31 do not necessarily need to be employed in the tires of a four-wheeled vehicle, but may be employed in the tires of a vehicle having one to three wheels or five or more wheels.

DESCRIPTION OF THE REFERENCE NUMERALS

10 . . . Vehicle, 11 . . . ABS, 13 . . . Wheel Assembly, 14 . . . Vehicle Wheel, 15 . . . Tire, 17 . . . Tire Valve, 18 . . . Valve Stem, 30 . . . Tire Condition Monitoring Apparatus, 31 . . . Sensor Unit, 41 . . . Sensor Unit Controller, 42 . . . Pressure Sensor, 43 . . . Temperature Sensor, 44 . . . Acceleration Sensor, 45 . . . Capacitance Sensor, 46 . . . RF Communication Circuit, 48 . . . Battery, 60 . . . Receiver Unit.

What is claimed is:

1. A wheel assembly rotational position identifying apparatus, which is provided in a wheel assembly of a vehicle to identify a rotational position of the wheel assembly, the apparatus comprising:
    an acceleration detector, which is configured to detect an acceleration that changes in accordance with the rotational position of the wheel assembly;
    a control section, which is configured to identify the rotational position of the wheel assembly based on the acceleration detected by the acceleration detector; and
    a battery, which is a power source for the wheel assembly rotational position identifying apparatus, wherein
    the control section is configured to operate in a control mode that is a selected one of a normal mode, in which the rotational position of the wheel assembly is allowed to be identified, and a power saving mode, in which a power consumption associated with identification of the rotational position of the wheel assembly is smaller than that in the normal mode,
    the control section is configured to switch the control mode to the normal mode when an initiation condition is met in accordance with an input from outside, and
    the control section is configured to switch the control mode to the power saving mode when a termination condition is met in the normal mode.

2. The wheel assembly rotational position identifying apparatus according to claim 1, wherein the termination condition is met when a specified time has elapsed since the vehicle started moving.

3. The wheel assembly rotational position identifying apparatus according to claim 1, further comprising a property detector, which is configured to detect an electrical property of a valve stem provided in the wheel assembly,
    the initiation condition is met in response to an amount of change in the electrical property of the valve stem detected by the property detector exceeding a reference change amount.

4. The wheel assembly rotational position identifying apparatus according to claim 1, wherein
    the control section is configured to execute a process based on an input from outside when the vehicle is in a stopped state, and
    the control section is configured not to execute a process based on an input from outside when the vehicle is moving.

5. The wheel assembly rotational position identifying apparatus according to claim 3, wherein
    the control section is configured to execute a detection process through the property detector when the vehicle is in a stopped state, and the control section is configured not to execute the detection process through the property detector when the vehicle is moving.

6. The wheel assembly rotational position identifying apparatus according to claim 1, wherein the control section is configured to identify the rotational position of the wheel assembly less frequently in the power saving mode than in the normal mode.

7. The wheel assembly rotational position identifying apparatus according to claim 1, wherein the control section is configured not to identify the rotational position of the wheel assembly in the power saving mode.

\* \* \* \* \*